(12) United States Patent
Bresciani et al.

(10) Patent No.: US 11,119,041 B2
(45) Date of Patent: Sep. 14, 2021

(54) MONITORING DISSOLUTION OF A DOSAGE FORM IN PROGRESS DURING DISSOLUTION BY LOW COHERENCE INTERFEROMETRY

(71) Applicant: Research Center Pharmaceutical Engineering GmbH, Graz (AT)

(72) Inventors: Massimo Bresciani, Graz (AT); Daniel Markl, Feldkirchen bei Graz (AT); Annalisa Mercuri, Ascoli Piceno (IT); Johannes Khinast, Graz (AT); Thomas Klein, Kindberg (AT)

(73) Assignee: Research Center Pharmaceutical Engineering GmbH, Graz (AT)

( * ) Notice: Subject to any disclaimer, the term of this patent is extended or adjusted under 35 U.S.C. 154(b) by 129 days.

(21) Appl. No.: 16/087,057

(22) PCT Filed: Mar. 21, 2017

(86) PCT No.: PCT/EP2017/056718
§ 371 (c)(1),
(2) Date: Sep. 20, 2018

(87) PCT Pub. No.: WO2017/162682
PCT Pub. Date: Sep. 28, 2017

(65) Prior Publication Data
US 2019/0391076 A1    Dec. 26, 2019

(30) Foreign Application Priority Data

Mar. 21, 2016   (GB) ..................................... 1604744

(51) Int. Cl.
*G01N 21/47* (2006.01)
*G01B 9/02* (2006.01)
(Continued)

(52) U.S. Cl.
CPC ..... *G01N 21/4795* (2013.01); *G01B 9/02091* (2013.01); *G01N 21/45* (2013.01);
(Continued)

(58) Field of Classification Search
CPC .. G01B 9/0209; G01B 9/02091; G01N 21/45; G01N 21/4795; G01N 21/8507;
(Continued)

(56) References Cited

U.S. PATENT DOCUMENTS 6,174,497 B1 * 1/2001 Roinestad .............. G01N 13/00
366/142
6,558,957 B1   5/2003 Roinestad et al.
(Continued)

FOREIGN PATENT DOCUMENTS

EP    1 436 610 B1   6/2006
EP    1 853 874 B1   9/2009
(Continued)

OTHER PUBLICATIONS

Fang, J.B., et al., Development and application of a biorelevant dissolution method using USP apparatus 4 in early phase formulation development. Mol. Pharm. 7, 2010, pp. 1466-1477.
(Continued)

*Primary Examiner* — Michael A Lyons
(74) *Attorney, Agent, or Firm* — Robert A. Blaha; Smith Tempel Blaha LLC

(57) ABSTRACT

A method of monitoring a property of a dissolution of an at least partially solid dosage form during a dissolution process is disclosed. The method includes at least partially dissolving the dosage form, and during the dissolution of the dosage form, simultaneously monitoring the property of the dissolution of the dosage form in progress by low coherence interferometry.

18 Claims, 5 Drawing Sheets

(51) Int. Cl.
G01N 21/45 (2006.01)
G01N 21/85 (2006.01)
G01N 33/15 (2006.01)
G01N 13/00 (2006.01)
G01N 21/84 (2006.01)
G01N 33/00 (2006.01)

(52) U.S. Cl.
CPC ........ *G01B 9/0209* (2013.01); *G01N 21/8507* (2013.01); *G01N 33/15* (2013.01); *G01N 2013/006* (2013.01); *G01N 2021/8416* (2013.01); *G01N 2033/0077* (2013.01); *G01N 2033/0096* (2013.01)

(58) Field of Classification Search
CPC ............. G01N 33/15; G01N 2013/006; G01N 2033/0077; G01N 2033/0096
See application file for complete search history.

(56) References Cited

U.S. PATENT DOCUMENTS

| | | | |
|---|---|---|---|
| 2004/0027569 A1 | 2/2004 | Tucker | |
| 2006/0262321 A1 | 11/2006 | De Groot | |
| 2008/0165354 A1 | 7/2008 | Rantanen et al. | |
| 2009/0185187 A1* | 7/2009 | Crist | G01N 21/8507 356/436 |
| 2011/0026010 A1* | 2/2011 | Walker | G01N 21/4795 356/51 |
| 2014/0193466 A1 | 7/2014 | Lawrence et al. | |
| 2014/0322429 A1* | 10/2014 | Markl | G01B 9/02091 427/2.14 |
| 2018/0231446 A1* | 8/2018 | Svanback | B01F 5/006 |

FOREIGN PATENT DOCUMENTS

| | | |
|---|---|---|
| EP | 2 799 842 A1 | 11/2014 |
| GB | 2446026 A | 7/2008 |
| WO | WO 1997046860 A2 | 12/1997 |
| WO | WO 2003098199 A1 | 11/2003 |
| WO | WO 2009021092 A1 | 2/2009 |
| WO | WO 2015070262 A1 | 5/2015 |

OTHER PUBLICATIONS

Farrugia, C. A. et al. Flow-Through Dissolution Testing A comparison with stirred beaker methods Figure I: 2002; pp. 17-19.
Fotaki, N., Flow-through cell apparatus (USP Apparatus 4): Operation and features. Dissolution Technol. 18, 2011, pp. 46-49.
Fyfe, C. A. et al. NMR imaging investigations of drug delivery devices using a flow-through USP dissolution apparatus. J. Control. Release 68, 2000, pp. 73-83.
Kakhi, M.; Classification of the flow regimes in the flow-through cell. European Journal of Pharmaceutical Sciences, (Apr. 18, 2009); pp. 531-544.
Markl, D. et al., In-Line Monitoring of a Pharmaceutical Pan Coating Process by Optical Coherence Tomography. Int. J. Pharm.; 2015.
Markl, D., et al., Optical coherence tomography as a novel tool for in-line monitoring of a pharmaceutical film-coating process. Eur. J. Pharm. Sci. 55, 2014, pp. 58-67.
Østergaard, J., et al., Simultaneous UV imaging and Raman spectroscopy for the measurement of solvent-mediated phase transformations during dissolution testing. J. Pharm. Sci. 103, 2014, pp. 1149-1156.
Rohrs, B.R., Calibration of the USP 3 (Reciprocating Cylinder) Dissolution Apparatus 3, 1997.
Thermo Fisher Scientific. (Aug. 3, 2010). www.thermoscientific.com/tc. Retrieved Nov. 19, 2014 from www.idealvac.com/files/brochures/Thermo_A25_Bath_Circulator.pdf.
Uddin, R., et al., Dissolution and Dissolution Apparatus: A Review. Int. J. Curr. Biomed. Pharm. Res. 1, 2011, pp. 201-207.
United States Pharmacopoeia, 711 Dissolution. USP Dissolution 1, 8; 2011.
Van Der Weerd, et al., Combined approach of FTIR imaging and conventional dissolution tests applied to drug release. J. Control. Release 98, 2004; pp. 295-305.
Van Der Weerd, et al., Release of poorly soluble drugs from HPMC tablets studied by FTIR imaging and flow-through dissolution tests. J. Pharm. Sci. 94, 2005, pp. 2096-2109.
Wang, Q.X., et al., Biorelevant dissolution: Methodology and application in drug development; 2009; pp. 6-12.
Yassin, S., et al., Diffusion and Swelling Measurements in Pharmaceutical Powder Compacts Using Terahertz Pulsed Imaging. J. Pharm. Sci.; 2015; n/a-n/a.
Zeitler, J.A., et al., In-vitro tomography and non-destructive imaging at depth of pharmaceutical solid dosage forms. Eur. J. Pharm. Biopharm. 71, 2009; pp. 2-22.
Donnely R.F. et al., "Optical Coherence Tomography is a Valuable Tool in the Study of the Effects of Microneedle Geometry on Skin Penetration Characteristics and in Skin Dissolution," Journal of Controlled Release 147 (2010), pp. 333-341.
Crist, B. et al., Evaluation of Induced Variance of Physical Parameters on the Calibrated USP Dissolution Apparatus 1 and 2; Dissolution Technologies, Feb. 2005; pp. 28-31.
Crist, G.B., Considerations for automating the dissolution test. Dissolution Technol. May 20, 2013, pp. 44-47.
Dorozynski, P.P. et al.; Novel application of MRI technique combined with flow-through cell dissolution apparatus as supportive discriminatory test for evaluation of controlled release formulations. AAPS PharmSciTech 11, 2010; pp. 588-597.
European Pharmacopeia 5.0, 20903E_Dissolution Test for Solid Dosage Forms; Jan. 2005; pp. 1-3.
Anonymous: "Dosage form—Wikipedia", Jan. 16, 2020 (Jan. 16, 2020), pp. 1-3, XP055663594, Retrieved from the Internet: URL:https://en.wikipedia.org/wiki/Dosage_form [retrieved on Jan. 30, 2020].
Anonymous: "Intradermal injection—Wikipedia", Jan. 20, 2020 (Jan. 20, 2020), pp. 1-3, XP055663613, Retrieved from the Internet: URL:https://en.wikipedia.org/wiki/Intradermal_injection#Intradermic_needles [retrieved on Jan. 30, 2020].
Garland, M.J. et al: "Influence of skin model on performance of drug-loaded soluble microneedle arrays", International Journal of Pharmaceutics, Elsevier NL, vol. 434, No. 1, May 25, 2012 (May 25, 2012), pp. 80-89, XP028428034, ISSN: 0378-5173, DOI: 10.1016/J.IJPHARM.2012.05.069 [retrieved on Jun. 2, 2012].
Duijs, Eric; Communication Pursuant to Article 94(3) EPC in Application No. 17712494.8; dated Feb. 11, 2020; pp. 1-12; Examining Division European Patent Office, 80298 Munich Germany.

* cited by examiner

MONITORING DISSOLUTION OF A DOSAGE FORM IN PROGRESS DURING DISSOLUTION BY LOW COHERENCE INTERFEROMETRY

TECHNICAL FIELD

The invention relates to a method of monitoring a property of a dissolution of a dosage form during a dissolution process.

Moreover, the invention relates to an apparatus for monitoring a property of a dissolution of a dosage form during a dissolution process.

TECHNOLOGICAL BACKGROUND

EP 2799842 A1 discloses a method of and a device for monitoring a property of a coating of a solid dosage form. The device comprises a coating apparatus configured for forming the coating on the solid dosage form, and a monitoring apparatus configured for monitoring the property of the coating of the solid dosage form in process, wherein at least a part of the monitoring apparatus is located so as to have insight in an interior of the coating apparatus, the interior accommodating the solid dosage form to be coated and a precursor for forming the coating, and wherein the monitoring apparatus is configured for monitoring the property or the coating of the solid dosage form simultaneously with and during a coating process using low coherence interferometry.

The dissolution of dosage forms is regulated under the European or United States Pharmacopoeia, which defines requirements for the qualitative and quantitative composition of dosage forms. In order to determine a dissolution property, information indicative of a dissolution process may be measured after the dissolution process.

SUMMARY

There may be a need to obtain a deeper understanding of a dissolution process.

According to an exemplary embodiment of the invention, a method of monitoring a property of a dissolution and/or a dispersion of an at least partially solid dosage form during a dissolution process is provided. The method comprises at least partially dissolving, dispersing or disintegrating the dosage form, and, during the dissolution of the dosage form, simultaneously monitoring the property of the dissolution of the dosage form in progress by low coherence interferometry.

According to a further exemplary embodiment of the invention, a device for disintegrating and subsequently dissolving a dosage form and for monitoring a property of the dissolution of the dosage form during a dissolution process is provided. The device comprises a dissolution apparatus configured for at least partially disintegrating and subsequently partially dissolving the dosage form, and a monitoring apparatus configured for monitoring the property of the dissolution of the dosage form during dissolving the dosage form by the dissolution apparatus, wherein the monitoring apparatus is configured for monitoring of the property of the dissolution of the dosage form simultaneously with and during a dissolution process using low coherence interferometry.

Hence, exemplary embodiments of the invention provide an apparatus for and a method of monitoring main factors which are involved (and relevantly involved) in a dispersion and a solubilization of dosage forms and/or intermediates during an in vitro dissolution test and/or a dissolution process. Exemplary embodiments of the invention allow for a deeper understanding of a dissolution process and the components of the dissolution process relating to a solid dosage form and/or intermediates.

OVERVIEW OF EMBODIMENTS

The term "at least partially solid dosage form" may particularly denote a dosage form which is partially or completely solid (in particular which comprises at least a solid outer shell) which is adapted to be administered to a human or an animal. For example, the at least partially solid dosage form may be a tablet having a solid outer shell and a liquid core. Further, the at least partially solid dosage form may be entirely solid. In particular, the solid dosage form may be a tablet, a pellet, a bead, a pill, a capsule, or a suppository. Further, the solid dosage form may comprise an active drug component such as an active pharmaceutical ingredient and/or a nondrug component. The nondrug component may for example be an excipient. For example, the solid dosage form may be a pharmaceutical drug, a dietary supplement, and/or a food product.

The term "dissolution" may particularly denote a process by which an original state of an at least partially solid dosage form becomes solutes (such as one or more dissolved components), thereby forming a solution of the previously at least partially solid dosage form in an original solvent. The process of dissolution of an at least partially solid dosage form may involve disintegration of the at least partially solid dosage form, in particular such that separate atoms, ions or molecules are released.

Further, the process of dissolution may involve a break up of bondings between particles, granules and/or agglomerates of the dosage form during the dissolution, when the dosage form comes into contact with the dissolution medium.

The term "property of a dissolution" may particularly denote any measurable attribute of a dissolution. For example, a property of a dissolution may be a diffusion behavior of the dosage form during dissolution, a swelling kinetics of the dosage form during dissolution, a disintegration behavior of the dosage form during dissolution, a thickness variation of a coating during dissolution, a thickness variability of a coating during dissolution, etc.

Further the property of dissolution may be a liquid ingress of the dissolution medium into the dosage form and/or a liquid penetration which may define how a liquid penetrates the dosage form.

The term "low coherence interferometry" or "LCI," may particularly denote an interferometry method which exploits the special properties of light having a low coherence. Examples for low coherence interferometry may be white light interferometry (WLI) and optical coherence tomography (OCT). Typically, a light source with high spatial and low temporal coherence may be employed. Particular examples for suitable light sources may include, among others, superluminescence diodes, femtosecond lasers, and supercontinuum lasers. In special applications also tunable laser sources may be applied.

According to an exemplary embodiment of the invention, the monitoring of a property of the dissolution during the dissolution of the dosage form may be performed by a monitoring apparatus configured for monitoring the property. In particular, the monitoring apparatus may be located in such manner that the dosage form can be monitored while the dissolution process of the dosage forms takes place or is still in progress. Further, the monitoring apparatus may be configured for monitoring the property of the dissolution of the dosage form simultaneously with and during a dissolution process. Moreover, the monitoring apparatus may be adapted in such a way that the property of the dissolution may be monitored or measured during the dissolution of the dosage form in the dissolution apparatus. In other words, it may be rendered unnecessary to interrupt a dissolution process or to finish the dissolution in order to monitor, to study or determine a property of the dissolution and/or the dissolution behavior. In particular, it may be an advantage of the described method and device that a property of a dissolution and/or a dissolution behavior can be monitored or determined while the process dissolving the dosage form is still in progress. Thus, it may be possible to ensure that a dissolution process is continued until a property of the dissolution and/or the dissolution behavior fulfills a predefined criterion. Further, the described method may provide the advantage that a reference model may be omitted and the property of the dissolution and/or the dissolution behavior may be directly determined during the process dissolving the dosage form. This may provide the advantage that an overall quality of the dissolution properties of a dosage form can be increased and the quality of a dissolution of a dosage form can be ensured. For instance, the dissolution properties of an at least partially solid dosage form used for pharmaceutical applications can have an impact on the speed and rate of release of a pharmaceutically active substance in the at least partially solid dosage form, which can hence be monitored and characterized as well according to exemplary embodiments of the invention.

Further, the device for disintegrating and subsequently dissolving a dosage form and for monitoring a property of the dissolution of the dosage form during a dissolution process may be embodied as a device for being applied in an in process real-time control or even quality control for real-time release in support of regulatory filing and/or manufacturing and control (CMC) of relevant comments such as investigational medicinal product dossier (IMPD), investigational new drug (IND), etc.

In particular, low coherence interferometry may allow monitoring a property of a dissolution and/or a dissolution behavior without influencing the dissolution process. More particularly, low coherence interferometry may be advantageously used as a non-invasive technique for determining or monitoring a property of a dissolution of a dosage form. Low coherence interferometry uses the wave superposition principle to combine light waves, particularly light waves that are modified by the at least partially solid dosage form to be analyzed, in a way that will cause the result of their combination to extract information from those instantaneous wave fronts. The basic working principle is as follows: when two waves are combined, the resulting wave pattern may be determined by the phase difference between the two waves. In particular, waves that are in phase will undergo constructive interference while waves that are out of phase will undergo destructive interference. Applying this principle to the characterization of a dissolution process of an at least partially solid dosage form enables the dissolution process to remain undisturbed so as to obtain meaningful information.

Next, further exemplary embodiments of the method and the device will be explained.

According to an exemplary embodiment, the low coherence interferometry comprises one of the group consisting of a white light interferometry, and an optical coherence tomography.

As noted above, low coherence interferometry is an interferometry technique which makes use of the wave superposition principle to combine waves in a way that will cause the result of their combination to extract information from those instantaneous wave fronts. The basic working principle is as follows: when two waves combine, the resulting wave pattern may be determined by the phase difference between the two waves. In particular, waves that are in phase will undergo constructive interference while waves that are out of phase will undergo destructive interference. In particular, optical coherence tomography may refer to a two or three dimensional imaging technique, while low coherence light interferometry and white light interferometry may refer to a one dimensional imaging technique. The optical setup for low coherence interferometry such as white light interferometry or OCT may comprise an interferometer, for example a Michelson type interferometer. However, also other types of interferometers, such as a Mach-Zehnder interferometer or a Sagnac interferometer, may be employed. More particularly, the light of the light source may be split into a reference and a sample arm and recombined after the light beam in the sample arm has been modified by the sample. The light of the reference arm and the sample arm may interfere with one another when the light beams are recombined. The recombined light may be used to analyze a property of the at least partially solid dosage form during the dissolution procedure. Alternatively, an autocorrelation signal may be used to analyze the property of the at least partially solid dosage form during the dissolution procedure. The autocorrelation signal may result from an interference of light reflected from different positions of the at least partially solid dosage form during the dissolution procedure. Thus, a reference arm of the interferometer may alternatively be omitted.

As mentioned above, optical coherence tomography may refer to a two or three dimensional imaging technique, while low coherence light interferometry and white light interferometry may refer to a one dimensional imaging technique. Therefore, the property of dissolution may be monitored in one, two or three spatial dimensions. In particular, monitoring the property of the dissolution in one spatial dimension may allow for a particularly fast and efficient determining of the property. However, in case a higher accuracy of the monitoring is necessary, the property of the dissolution may also be monitored in two or three spatial dimensions. Depending on the property to be monitored, it may be particularly necessary to monitor the property in more than one spatial dimension.

In particular, a depth-resolved OCT signal may be acquired by any suitable variant of OCT such as Frequency-domain OCT, e.g. spectral-domain OCT and swept-source OCT, or time-domain OCT.

In time-domain OCT, a reference arm in the interferometer may be varied, particularly by moving a mirror in the reference arm. A signal may only be detected when the photons reflected from both interferometer arms, i.e. the reference arm and a signal or measurement arm, have travelled the same optical distance to a detector. Particularly, mechanical instabilities of an interferometer setup and noise may be induced by the mechanical movement of the mirror in the reference.

The OCT signal acquisition in Fourier-domain OCT may offer advantages in terms of imaging speed and sensitivity and may thus enable the application of OCT as an in-line monitoring method or in process monitoring method. In Fourier-domain OCT, the reference arm of the interferometer may be fixed and the interference signal of back-reflected and back-scattered light from the reference mirror and the sample may be detected in a spectrally resolved way. This may either be performed in parallel (spectral-domain OCT) by using a dispersing element and a CCD or CMOS camera or sequentially (swept-source OCT) by scanning a narrow laser line over a broad spectral region. In both embodiments the depth information may be accessed by applying an inverse Fourier transform on the acquired interference spectrum.

The employed light source may be chosen in dependence with the employed imaging technique and in dependence of the analyzed at least partially solid dosage form. For example, time-domain OCT and spectral-domain OCT may employ a light source having a broad bandwidth while swept-source OCT may employ a light source having a smaller or narrower bandwidth, which can be swept in wavelength over a rather large range.

According to an exemplary embodiment, the property of the dissolution and/or a not yet fully dissolved portion of the at least partially solid dosage form is monitored by analyzing an obtained interference pattern of the low coherence interferometry.

In particular, analyzing the obtained interference pattern or obtained signal may depend on the employed variant of LCI. The interference may cause a modulation in the detected or obtained signal. In case of time-domain OCT, an intensity of the signal may be modulated in time. Correspondingly, an intensity of the obtained signal may be modulated in frequency in case of Fourier-domain OCT. A frequency of the modulation may be a function of a difference of a path length between the two interferometer arms. Thus, the frequency of the modulation may describe the depth from which the light may be scattered.

According to an exemplary embodiment of the invention, the property of the dissolution is at least one of the group consisting of a diffusion behavior of the dosage form during dissolution, a swelling kinetics of the dosage form during dissolution, a swelling of a coating during dissolution, a porosity of the dosage form during dissolution, a structural change of the dosage form during dissolution, a disintegration behavior of the dosage form during dissolution, a water penetration behavior of the dosage form during dissolution, a thickness reduction of a coating of the dosage form during the dissolution, a thickness variation of a coating of the dosage form during dissolution, a thickness variability of a coating of the dosage form during dissolution, an erosion of a coating of the dosage form during dissolution, an erosion of a core of the dosage form during dissolution, a dissolution of particles of a core of the dosage form during dissolution, a formation of a gel layer during dissolution, a formation of an osmotic layer during dissolution, a release of active pharmaceutical ingredient of the dosage form during dissolution, a breaking of a shell of the dosage form during dissolution, a wetting of powder of the dosage form during dissolution, a dispersion behavior during dissolution, a release of liquid content of the dosage form during dissolution, a self-emulsification of at least part of the dosage form during dissolution, a permeation of dissolution medium into the dosage form during dissolution, a diffusion of a drug substance of the dosage form into a dissolution medium, and a cracking behavior of a coating of the dosage form during dissolution.

In particular the individual properties mentioned above will be explained in more detail from which the interaction occurring between the aqueous medium and the dosage forms can be analyzed. A diffusion behavior of the dosage form may be the general behavior how the dosage form changes its appearance under the influence of a dissolution medium over a certain period of time. A swelling kinetics may be a behavior of the whole dosage form when it may soak up the dissolution medium, such that it increases its range or volume. The swelling kinetics of the core of the dosage form may be the same behavior as the swelling kinetic behavior of the dosage form which only relates to the core of the dosage form. Vice versa the swelling kinetics of the coating may be the behavior of only of the coating of the dosage form when it is soaked up with the dissolution medium. A porosity of the dosage form may be the behavior, how the dosage form changes its permeability and structural matrix during the dissolution. A structural change of the dosage form may be information about the texture, pattern and/or composition of the dosage form and it changes during the dissolution after predetermined time interval and/or from the beginning of the dissolution. A disintegration behavior may the behavior how the dosage form is dissolved, which part is dissolved first in which range and which time. With a water penetration behavior may be analyzed how water penetrates the dosage form, in particular the coating and the core of the dosage form. Further which substances of the dosage form may be resistant to water or not. With the thickness reduction of a coating is observed the decreasing of the coating during the time under the influence of the dissolution medium. Certain substances of dissolution media may be analyzed how they affect the decreasing of the coating or not. By analyzing the thickness variation, the differences in the thickness of the coating may be observed, such that it will be visualized how uniform or non-uniform the thickness is decreased during dissolution. By analyzing the thickness variability the up and downs of the coating thickness may be observed, whether the thickness is reduced uniform or whether the thickness is increased and then decreased by the influence of the dissolution medium. With the analysis of the erosion of a coating it may be observed how the coating is worn away, which parts of the coating are removed first, such that it can be visualized which parts are more stable against the dissolution medium. An erosion of a core of the dosage form may be a removing behavior of the inside of the dosage form like the erosion behavior of the core. With a dissolution of core particles of the dosage form may be analyzed how this core particles dissolves in a certain time. A formation of a gel layer may be the behavior of a part or a layer of the dosage form, for example the coating of the dosage form, wherein the substances of the layer forming a gel layer with the dissolution medium. A formation of osmotic layer may be a forming of a partially permeable layer of a part of the dosage form. A release of active pharmaceutical ingredients may be observed during the dissolution, such that it may be analyzed how the ingredients dissolve from the dosage form into the dissolution medium. A dosage form shell breaking may be a behavior of for example a hard shell which protects the dosage form and how this shell is removed, in particular breaks by the influence of the dissolution medium. By analyzing a wetting of powder it may be observed how the powder is absorbing the dissolution medium until the powder is fully wet. By analyzing a dispersion behavior it may be observed how the particles and substances of the dosage form spread or disperse into the dissolution medium in a certain speed and time. A release of liquid content of a dosage form may be observed, such that it may be visualized how the liquid content leaves the dosage form and how it is dissolved in the dissolution medium. A self-emulsification behavior may be a behavior of a substance which is forming an emulsion by the influence of the dissolution medium, such that the forming of the emulsion may be analyzed. A permeation of the dissolution medium into the dosage form may be the diffusion or the ingress of the dissolution medium into the dosage form. By analyzing a diffusion of a drug substance of the dosage form into a dissolution medium it may be observed how fast and in which time and in which distribution the drug substance is diffused into the dissolution medium. A cracking behavior of a coating of the dosage form may be the behavior whether or how the coating breaks by the influence of different dissolution media and the build-up of hydrostatic pressure inside the dosage form.

This parameters may be investigated for at least one dosage form consisting of at least one of the group comprising an immediate release tablet, a orodispersable tablet, a modified release tablet, in particular a tablet of a erodible matrix, a osmotic tablet (push and pull tablet), other matrix tablets, and gastric retentive tablets; a multiparticulate system, in particular a granule, a powder, a microcapsule, and a pellet; a capsule, in particular a hard capsule, and a soft capsule; a gel, in particular a hydrogel, pates, creams, suppositories, pessaries, films, and patches; a drug delivery system, in particular a solid, a liquid, a semisolid and a self-emulsifying drug delivery system; an implant, a polymeric matrix, an extrudate and an intravaginal ring.

For example, it may be necessary to ensure a certain dissolution of a dosage form in order to ensure a particular quality feature of a dosage form, such as permeation of the dissolution medium into the dosage form, drug diffusion out of the dosage form, swelling kinetics of the dosage form, erosion behavior of the dosage form, cracking behavior of the dosage form during dissolution. Furthermore, a homogeneity of the dissolution may also improve the quality of the dissolution behavior of the dosage form. Depending on the material and/or substance of the dosage form it may be advantageous to monitor how a dosage form dissolves in the dissolution apparatus. In particular, in some case it may be necessary to monitor a dissolving characteristic of a dosage form during the dissolution process in order to ensure the quality of a dosage form.

According to an exemplary embodiment, the dosage form is one of the group consisting of a tablet, in particular one of an immediate release tablet, an orodispersable tablet, a modified release tablet, an osmotic tablet, a semisolid tablet, a self-emulsifying tablet, a multilayer tablet, and a gastric retentive tablet, a granulate, a powder, a microcapsule, a pellet, a capsule, in particular one of a hard capsule, and a soft capsule, a gel, in particular a hydrogel, a paste, a cream, a suppository, a pessary, a film, a patch, an implant, a polymeric matrix, and an extrudate.

In particular, the dosage form may be of different types, such that the monitoring of the property of the dissolution may be conducted at a variety of dosage forms. This may allow for monitoring and determining the behavior of different types of dosage forms. Also this may allow for comparing the different dissolution behaviors of the different dosage forms. In other words, the dissolution property may be monitored and determined for all types of dosage forms and not only for one single type of dosage form.

According to an exemplary embodiment the property of the dissolution is monitored in a contactless manner.

In particular, there is no need for the monitoring apparatus to be in direct contact with the dosage form. This may allow for non-destructing monitoring and measuring of the property of a dissolution. Thus, the dissolution of the dosage form is not disturbed or destroyed with the method for monitoring of the property of the dissolution. Hence, meaningful results without artefacts may be obtained.

According to an exemplary embodiment, information indicative of the property is detected in a plurality of consecutive time intervals or continuously in time.

For example, information or images of the dissolution of the dosage form may be obtained at time intervals from the point when the dissolution is starting. For example, information or images of the dissolution of the dosage form may be obtained in a short measurement time, so that the information may be obtained substantially in real time. This allows for monitoring a part of a dissolution process or monitoring the whole dissolution process. This allows for monitoring the property of the dissolution of the dosage form in situ. The term "in situ" may denote the monitoring of the property of the dissolution while the dissolution is in progress. Thus, the whole course of action of the dissolution procedure (rather than only a starting point and an end point) may be monitored.

According to an exemplary embodiment, the monitoring is conducted in the framework of a dosage form manufacturing process of monitoring manufacturing quality.

For example the monitoring may be conducted after the manufacturing process of the dosage form for determining a quality feature of the dosage form. This allow for ensuring a certain quality of the dissolution of the dosage form during manufacturing. It is however also possible that a manufacturing process of manufacturing multiple dosage forms is carried out, and individual ones (for example one of thousand) of the manufactured dosage forms are discharged from the manufacturing line for monitoring quality of the manufacturing process. If the analysis should yield the result that the quality of the manufactured dosage forms is insufficient in view of its dissolution properties, the manufacturing parameters may be adapted accordingly.

According to an exemplary embodiment, the monitoring is conducted while the dosage form is changing a dosage form constitution.

In particular the monitoring is conducted during the dissolution of the dosage form while the dosage form changes its three-dimensional structure. This allows for monitoring the dosage form while the dosage form changes its composition. Thus properties of the dissolution behavior as the structural change and the change in the composition may be monitored and determined. The changing constitution may be monitored and determined with increasing time while the dissolution process is in progress.

In an embodiment, the monitoring is conducted by an in-line process. In the context of the present application, the term "in-line process" may particularly denote a measurement where the sample (i.e. the dosage form under analysis) is not removed from the process stream during the analysis (and which can be invasive or noninvasive). The process of removing the sample may be denotes as "off-line" process, where the sample is analyzed outside the dissolution system (not in situ). In contrast to this, the term "on-line" denotes a measurement where the sample is diverted from the manufacturing process, and may be returned to the process stream. Moreover, the term "at-line" denotes a measurement where the sample is removed, isolated from, and analyzed in close proximity to the process stream. Although exemplary embodiments of the invention are also compatible with an on-line process or an at-line process, execution of the method in terms of an in-line process is particularly preferred, because this allows to obtain the desired information (in particular simultaneously with a dosage form manufacturing procedure) substantially without disturbing a process flow, substantially in real time and with a minimum time loss. According to an exemplary embodiment, at least a part of the monitoring apparatus is located so as to have insight into an interior of the dissolution apparatus, the interior accommodating the dosage form to be dissolved and comprising a volume in which the dissolving of the dosage form occurs.

In an embodiment, the method comprises correlating the monitored property of the dissolution with a pharmacokinetic characteristic. In particular, the monitored property of the dissolution according to an exemplary embodiment of the invention may facilitate or allow or even support as a validated methodology a correlation of a dissolution/dispersibility profile with pharmacokinetic (PK) outcomes or characteristics, such as a PK variability (e.g. variability of patients in their response to dosage forms), a low AUC (area under the curve, which determines the released concentration of the dosage form or the total dosage form exposure over time in the monitoring system/test liquid/human body), longer time to reach the peak plasma concentration of a drug after an administration (which describes the time in which the peak plasma concentration is monitored), the peak plasma concentration of a drug after administration, etc. With the correlation of the property of the dissolution with the pharmacokinetic characteristics the results obtained from the exemplary embodiment of the invention may be compared with the results of known pharmacokinetic characteristics of known dosage forms or new dosage forms. Therefore, a better understanding of the physical and physiological mode of action may be gained.

For example, at least a part of the monitoring apparatus may be located so as to have insight in an interior of the dissolution apparatus; particularly the monitoring apparatus may be located so as to have an insight in the dissolution apparatus through an aperture or an opening in the dissolution apparatus. In particular, the interior may accommodate the dosage form to be dissolved and also a dissolution unit for dissolving the dosage form. This may provide the advantage that the monitoring of the dissolution may be conducted without having refractions from other components of the device.

According to a further exemplary embodiment, the monitoring apparatus and the dissolution apparatus are configured for guiding primary electromagnetic radiation from the monitoring apparatus into the dissolution apparatus and for guiding secondary electromagnetic radiation, generated by an interaction between the primary electromagnetic radiation and the dosage form during dissolution, from the dissolution apparatus into the monitoring apparatus. For instance, a primary electromagnetic radiation beam may be directed from the monitoring apparatus through an optically transparent window of the dissolution apparatus, and a secondary electromagnetic radiation beam (generated in response to the primary electromagnetic radiation beam interacting with the at least partly solid and presently dissolving dosage form) may be able to propagate back through the optically transparent window (or another optically transparent window) to the monitoring apparatus for detection and data processing.

For example, this configuration allows for conducting the monitoring by an OCT. The primary electromagnetic radiation is getting in contact with the dosage form to be monitored. The primary electromagnetic radiation interacts with the dosage form and generates the secondary electromagnetic radiation, which will be guided back into the monitoring apparatus for receiving and determining the information about the dissolution of the dosage form. In particular, the monitoring apparatus may have an insight into the dissolution apparatus and may monitor and determine the dissolution property directly by the guided electromagnetic radiation.

According to an exemplary embodiment of the invention, the dissolution apparatus comprises at least one of the group consisting of a basket apparatus, a paddle apparatus, a reciprocating cylinder, a flow through cell, an intrinsic dissolution system, a Franz cell, and a membrane dissolution system.

For example the dissolution may be carried out with different dissolution systems. The choice of the dissolution apparatus for the specific dosage form may be influenced by the physical and/or chemical characteristics of the dosage form to be determined. All apparatus which may be used and which will be in contact with the sample, the dosage form or the dissolution medium, have to be inert. For ensuring no reaction with the sample during the dissolution process the apparatuses may be made of stainless steel or being coated with non-interfering material. The dissolution system may comprise a basket apparatus, which comprises a vessel with a hemispherical bottom made of glass or inert material, a fitted cover with a central hole for evaporation and a stirrer accommodated in the hole. The vessel may be immersed in a water bath, which maintains the temperature of the dissolution medium at $37\pm0.5°$ C. The dosage form may be located in the vessel in a mesh basket arranged at the lower end of the stirrer. The stirrer may be conducting rotational motions which will affect the dissolution. The mesh of the basket may be available in different sizes and dimensions for the different kind of dosage forms. Before the analysis the medium may be degassed for reducing the influence of bubbles. With this basket apparatus preferably tablets, capsules, beads, floaters, in particular immediate-release oral solid dosage forms, solid, monodisperse and polydisperse dosage forms may be analyzed. Further the dissolution apparatus may comprise a paddle apparatus. This paddle apparatus may comprise or consists of a vessel (like the vessel of the basket apparatus) and a metallic stirrer with a blade attached to the lower part of the stirrer. The shaft and the blade of the stirrer may be coated with inert material. A water bath maintains the temperature at $37\pm0.5°$ C. The rotational motion of the stirrer may affect the dissolution of the dosage form. Therefore, the shaft of the stirrer may be positioned with less than 2 mm deviation from the vertical axis of the vessel and may rotate without wobble. The dosage form may be placed on the bottom of the vessel. With this paddle apparatus preferably solid dosage forms, in particular tablets and capsules are analyzed. For floating dosage form a sinker device may be used. Further, for example the dissolution apparatus may comprise a reciprocating cylinder. Such an apparatus may also comprise or consist of a set of cylindrical glass vessels, a set of glass reciprocating cylinders and a motor placed vertically inside the vessel and which is used to reciprocate the cylinders. With the reciprocating cylinders and the dosage form placed therein, the dissolution may be conducted. The reciprocating cylinders may comprise screens placed at the top and the bottom of each cylinder. The reciprocating rate may be determined by the user and may be maintained by a device at a specific dip rate. The reciprocating cylinder may be immersed into thermostatic vessels (tempered by a water bath at a temperature of $37\pm0.5°$ C.) containing the dissolution medium. The dissolution medium is draining into the reservoir as the cylinder may be moving up and down Further, the dissolution apparatus may comprise a flow through cell, which may comprise or consist of a dissolution medium reservoir, a pump, a flow through cell and a water bath. The dosage form maybe placed in the flow through cell for dissolution. The pump may guarantees the pulsing rate through the flow through cell which may force the dissolution medium from the reservoir upwards into and through the flow through cell. The pump may provide a delivery range from 240 to 960 ml per hour and a flow rate between 4 to 16 ml/min. For protecting the dissolution system from vibrations of the pump the pump may be provided separately. For providing a pulsing and a non-pulsing flow a peristaltic and a pulsating piston may be used. For example, for achieving a pulsing flow of 120±10 pulses per minute and a sinusoidal profile a pulsating piston pump may be used. The flow through cell may be made of transparent and inert material and it may be mounted vertically. For preventing the loss of undissolved particles a filter system may be positioned at the top of the cell. These filters may be made of glass fiber or glass wool with different pore sizes. A water bath or a temperature control system may maintain the temperature at 37±0.5° C. Further, the dissolution apparatus may be a Franz cell, which may comprise or consist of a cap, a top, a donor chamber, a donor compartment, a clamp, a membrane and a body. Further, for example the dissolution apparatus may be a Transwell® dissolution system, which may comprise or consists of a membrane on which the dosage form is placed, an insert and a body. Transwell is a registered trademark of Corning Incorporated, Corning, N.Y., U.S.A. Further the dissolution apparatus may be a paddle over disc apparatus (USP 5), a cylinder apparatus (USP 6), a reciprocating holder apparatus (USP 7) and/or an intrinsic dissolution system.

For example, the dissolution apparatus may comprise a µDiss Profiler™, which may comprise or consist of three main parts, i.e. a UV spectrometer, fiber optics and vessels. µDiss Profiler is a trademark of Pion Inc. of Billerica, Mass. U.S.A. This dissolution apparatus may be a small volume dissolution testing apparatus.

In particular, for different types of dosage forms different dissolution apparatuses may be applied. This may provide the advantage that the dissolution of different dosage forms may be monitored and determined under different conditions and circumstances, specifically adapted to the needs of a respective application. Thus, different parameter may be applied to the dissolution of the dosage form, which may be monitored, determined and compared.

According to an exemplary embodiment, a medium in which the dosage form is dissolved during the dissolution process comprises at least one or more of the group consisting of water, one or more buffers, a biorelevant medium, and a viscous medium.

For example, the medium for dissolving the dosage form may comprise water, a buffer, biorelevant media or viscous media for simulating different dissolution conditions to which the dosage form is exposed.

In particular, the biorelevant media may simulate physiological conditions from which may obtained in vitro data during the monitoring. This data may be compared with in vivo results.

For example, with different types of dissolution media different conditions may be simulated, from which with the monitoring apparatus the properties of dissolution may be monitored and determined. These properties of the different dissolution media may be compared with each other and may be compared with data obtained from in vivo conditions to where the dosage forms are applied.

According to a further exemplary embodiment, the device comprises a flow through cell and an electromagnetic radiation supply element and configured for supplying electromagnetic radiation from a sensor head of the monitoring apparatus to the dosage form in the dissolution apparatus.

For example, the flow through cell may be adapted to comprise an electromagnetic radiation supply element, such as a hollow tube or a fiber optic element, which will guide the electromagnetic radiation to the dosage form. This allows for guiding the electromagnetic radiation directly to the dosage form without having high reflections. Further, this allows for directly monitoring the electromagnetic radiation obtained from the dosage form. This electromagnetic radiation supply element may enable insight into the dissolution apparatus. With the use of the flow though cell the dosage form may advantageously be fixed in the cell for the analysis by the OCT, because the sensor may analyze non-moving samples. The use of a basket apparatus may also be possible for analyzing non-moving samples by the OCT.

According to an exemplary embodiment, the electromagnetic radiation supply element extends from the sensor head to the dosage form.

In particular, the electromagnetic radiation supply element may have a range from the sensor head of the monitoring device to the dosage form. The specific range of the electromagnetic radiation supply element may depend on the optical system which is used in the monitoring apparatus. In particular different lenses have different focus points. Depending on this focus points, the range of the electromagnetic radiation supply element may be selected. After the selection of the range, the property of the dissolution may be monitored directly.

According to an exemplary embodiment, the electromagnetic radiation supply element extends through an opening of the flow through cell into the dissolution apparatus.

In particular the electromagnetic radiation supply element may extend through the outer and inner wall of the dissolution apparatus, such that the electromagnetic radiation supply element may be surrounded at the end, which extends into the dissolution apparatus, by the dissolution medium.

For example, the opening is a round hole or a round window. In particular, the opening may be sealed with at least one seal such that the dissolution medium does not leak out of the dissolution apparatus. In particular, the seal may be placed between the opening and the electromagnetic radiation supply element.

Further, the insight into the dissolution apparatus may be enabled with the electromagnetic radiation supply element which is close to the dosage form. This opening may reduce refractions which may occur when the electromagnetic radiation supply will extend just to the outer wall of the dissolution apparatus.

According to a further exemplary embodiment, the flow through cell comprises a transparent section, through which the monitoring apparatus has an insight into an interior of the dissolution apparatus.

For example, the transparent medium may be a transparent glass or a transparent membrane or a transparent plastic. The electromagnetic radiation supply element may be equipped with the transparent medium at the end side, which extends into the dissolution apparatus.

In particular, the transparent medium may prevent the dissolution medium to flow into the electromagnetic radiation supply element and thereby into the monitoring apparatus.

Further, the transparent medium may allow for having a direct insight into the dissolution apparatus. With the transparent medium, the electromagnetic radiation supply element may be located as close as possible at the dosage form.

According to an exemplary embodiment, the flow through cell has an inner diameter at a dosage form accommodation position in a range between 17 mm and 30 mm, or between 8 mm and 16 mm.

In particular, the flow through cell has an inner diameter at a dosage form accommodation position in a range between 20 mm and 25 mm, or between 10 mm and 14 mm.

For example a large or a small flow through cell may be used as dissolution apparatus. In particular, the large or the small flow through cell may be a flow through cell which is used according the requirements of the European Pharmacopeia or the US Pharmacopeia.

According to an exemplary embodiment, the dissolution apparatus comprises at least one pump for pumping at least one of a dissolution medium and a heating medium.

For example, the dissolution medium may be pumped through a flow through cell and the dissolution medium may need to be heated such that the temperature of the dissolution medium maintains at a specific range. Therefore, to maintain the temperature, a pump for pumping a heating medium may be applied.

According to an exemplary embodiment the device comprises a control unit (such as a processor, for instance a microprocessor or a central processing unit, CPU) adapted to perform the method. For example, the control unit may carry out the method using a correspondingly adapted software code.

For example the control unit may control the monitoring apparatus and/or the dissolution apparatus. Further the control unit may control the electromagnetic radiation, the electromagnetic radiation supply element, the pump for pumping dissolution medium and further.

The aspects defined above and further aspects of the invention are apparent from the examples of embodiment to be described hereinafter and are explained with reference to these examples of embodiment.

BRIEF DESCRIPTION OF THE DRAWINGS

The invention will be described in more detail hereinafter with reference to examples of embodiment but to which the invention is not limited.

DETAILED DESCRIPTION OF ILLUSTRATED EMBODIMENTS

Figure 1:
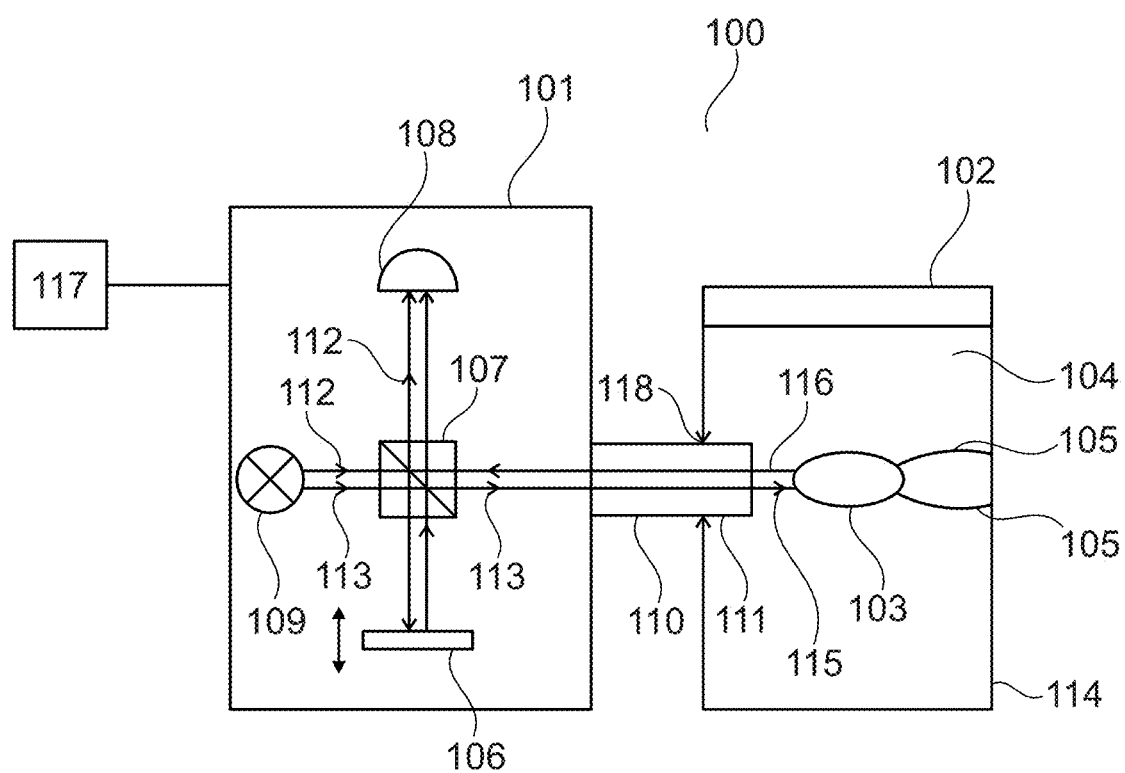
FIG. 1 illustrates a device for monitoring a property of a dissolution of an at least partially solid dosage form during a dissolution process according to an exemplary embodiment of the invention.

Before exemplary embodiments will be described by referring to the Figures some general aspects of the invention will be explained:

OCT systems may be applied in the pharmaceutical field as an imaging tool for a non-destructive analysis of dosage forms, in particular solid dosage forms. With the use of the OCT it is possible to analyze, observe and/or monitor the dissolution behavior and drug release kinetics of dosage forms in a high quality manner by the use of e.g. dimensional images from the OCT. Therefore different dissolution apparatuses may be used, as every USP apparatus.

The illustrations in the drawings are schematically presented. In different drawings, similar or identical elements are provided with the same reference signs.

In the following, referring to FIG. 1, a device 100 for dissolving a solid dosage form 103, here embodied as a pharmaceutical tablet, and for monitoring a property of a dissolution of the dosage form 103 in a liquid solution during a dissolution process according to an exemplary embodiment will be explained.

The device 100 comprises a dissolution apparatus 102 configured for at least partially dissolving the dosage form 103, and comprises a monitoring apparatus 101 configured for monitoring the property of the dissolution of the dosage form 103 during dissolving the dosage form 103 by the dissolution apparatus 102. In particular, the monitoring apparatus 101 is arranged in such a way that a part of the monitoring apparatus 101, i.e. an electromagnetic radiation supply element 110, extends into and is thus partly located in the dissolution apparatus 102. In the shown embodiment, the dissolution apparatus 102 contain a container or a vessel 114 in which the dosage form 103 may be introduced for dissolution. A portion of the electromagnetic radiation supply element 110 of the monitoring apparatus 101 or a part of it may be placed in a sensor window 118, a hole or a recess formed in a wall, a mantle or a shell of the vessel 114 of the dissolution apparatus 102. The monitoring apparatus 101 has an insight into dissolution apparatus 102 by this electromagnetic radiation supply element 110. The electromagnetic radiation supply element 110 extends into the dissolution apparatus 102 close to the dosage form 103. The electromagnetic radiation supply element 110 may be formed as a hollow tube, wherein electromagnetic radiation 115 may supplied from a sensor head 111 of the monitoring apparatus 101 to the dosage form 103. The range between the dosage form 103 and the sensor head may be below 25.1 mm according to exemplary embodiment of the invention. The range between the dosage form 103 and the sensor head 111 may also be higher than 25.1 mm, for example depending on the optical system 110 of the monitoring apparatus 101. The dosage form 103 may be fixed with a fixture 105 inside of the dissolution apparatus 102. For example, the fixture 105 of the dosage form 103 may be a clamp or a metallic mesh on which the dosage form 103 is placed. With this fixture 105, dosage form 103 may remain fixed during the dissolution. Inside of the dissolution apparatus 102, the dosage form 103 may dissolve in a dissolution medium 104. This dissolution medium 104 may comprise or consist of water, buffers, biorelevant media or a viscous media.

The monitoring apparatus 101 is configured for monitoring a disintegration behavior of the dosage form 103 during dissolution (and/or another property of the dissolution of the dosage form 103) simultaneously with and hence during a dissolution process using low coherence interferometry. In particular, the dissolution apparatus 102 may comprise a basket apparatus, a paddle apparatus, a reciprocating cylinder, a flow through cell, and/or an intrinsic dissolution system, a Franz cell, Transwell® dissolution system or a µDiss Profiler™.

The monitoring apparatus 101 comprises a light source 109, a detector 108, a reference mirror 106 and a beam splitter 107. The light of the light source 109 may be guided freely or may be coupled into an optical fiber. The light is guided towards the beam splitter 107, which is splitting the light beam into two separate optical paths 112 and 113. One optical path 113 is guided towards the electromagnetic radiation supply element 110 into the dissolution apparatus 102. The second optical path 112 is guided towards the beam splitter 107 at which the second optical path is reflected into the direction of the detector 108. The light which is travelling backwards from the dosage form 103 will be reflected by the beam splitter 107 and guided into the direction of the detector 108. With those two detected light beams the interference signal may be analyzed and the information about the monitored property of the dissolution may be extracted. For this purpose, image processing methods such as pattern recognition, etc., may be implemented.

The device 100 for monitoring a property of a dissolution of a dosage form 103 may be controlled and monitored by a control unit 117. This control unit 117 may be adapted for performing the monitoring of a property of a dissolution of a dosage form 103 and the control unit 117 may be used for control the parameters of the monitoring apparatus 101 and the dissolution apparatus 102.

Figure 2:
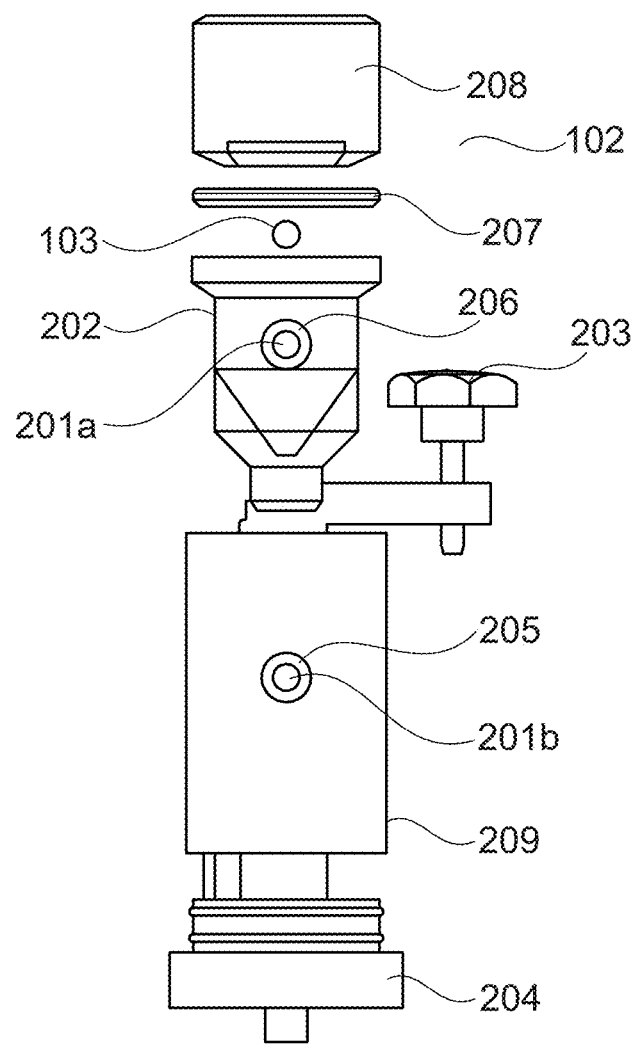
FIG. 2 shows a dissolution apparatus of a device according to an exemplary embodiment of the invention.

In the following, referring to FIG. 2, schematic of a dissolution apparatus 102 according to an exemplary embodiment of will be explained.

The dissolution apparatus 102 comprises an adapted flow through cell 202, which comprises the electromagnetic radiation supply element 110, which extends through an opening 201a of the dissolution apparatus 102 into the dissolution apparatus 102. Such a flow through cell 202 may be specifically configured for small refractions of the optical beam, which are induced by the wall of the flow through cell 202, the dissolution medium 104 and a heating medium. The electromagnetic radiation has to pass on its path to the dosage form a shell 209 of the flow through cell 202. The shell 209 comprises the heating medium which both influences the electromagnetic radiation. Further the electromagnetic radiation is influenced by the wall of the flow through cell 202 itself and the dissolution medium 104. For preventing such influences and for reducing refractions of the optical beam the flow through cell 202 is adapted according to the present invention by providing the electromagnetic radiation supply element 110. The flow through cell comprises a tube 110 as electromagnetic radiation supply element provider. This tube may be a hollow tube or maybe a tube comprising an optical fiber. For preventing a leakage of the dissolution medium 104 into the monitoring apparatus 101, the tube may be sealed by two O-rings. The end of the tube which extends into the dissolution apparatus 102 may be sealed by a foil, or maybe sealed by a transparent medium or glass. The tube may extend from the sensor head 111 to the dosage form 103. The tube is configured to supply electromagnetic radiation from the sensor head 111 of the monitoring apparatus 101 to the dosage form 103. Therefore, the tube extends from the sensor head 111 of the monitoring apparatus 101 to the dosage form 103. Further, the flow through cell 202 comprises an opening 201a which may be a sensor window, through which the electromagnetic radiation supply element 110 extends. The opening 201a is sealed by a sealing ring 206 against leakage. The flow through cell 202 may be surrounded by a shell 209, this shell 209 may also comprise a sensor window or opening 201b. This opening 201b of the shell 209 may also be sealed by a sealing ring 205 against leakage. For dissolving the dosage form 103, the dissolution medium 104 may be pumped by a pump through the flow through cell 202. In particular for maintaining a specific temperature of for example 37±0.5° C., the dissolution medium 104 may be heated by a heating system composed of a pump which pumps a heating medium through the space between the shell 209 and the flow through cell 202. Between the flow through cell 202 and a cell cover 208 an O-ring 207 is arranged, which separates and seals the heating circuit from the dissolution medium 104. In the cell cover 208 a different filter may be arranged according to the different dosage forms 103. Over this filter the dissolution medium 104 is removed from the flow through cell 202. The fixation of the adapted flow through cell 202 and its shell 209 comprises a connection bottom 204 and an adjusting screw 203. The connection bottom comprises a tube for the heating medium. Further with the connection bottom 204 the dissolution medium 104 is conducted and the circuit for the heating medium is closed. For including or removing of the flow through cell 202 the adjusting screw 203 may be used.

Figures 3A, 3B:
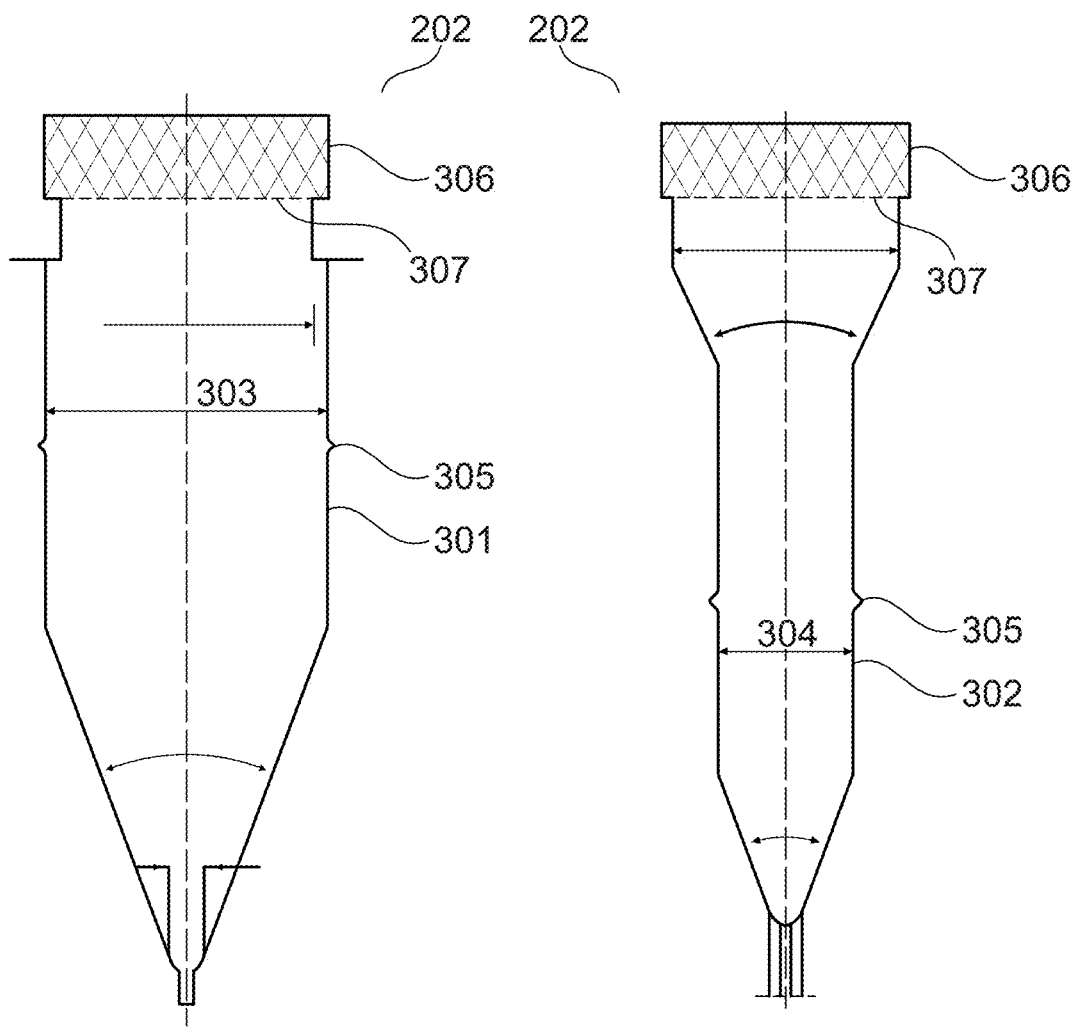
FIG. 3A illustrates a first flow through cell which may be implemented according to an exemplary embodiment of the invention.
FIG. 3B illustrates a second flow through cell which may be implemented according to another exemplary embodiment of the invention, wherein the second flow through cell is smaller than the first flow through cell according to FIG. 3A.

In the following, referring to FIG. 3A and FIG. 3B, a small 302 and a large flow through cell 301 according to an exemplary embodiment will be explained. For the use of a dissolution apparatus 102 it may be possible to choose between two (or more) variations of a flow through cell 202. Depending on the different kind of dosage forms the right flow though cell may be chosen. The first variant may be a large flow through cell 301 (FIG. 3A), which may have a larger inner diameter 303 than the small flow through cell 302 (FIG. 3B). In particular, the inner diameter 303 of the flow through cell 301 (FIG. 3A) at a dosage form accommodation position 305 may have a range between 17 mm to 30 mm. More particularly, the range of the inner diameter 303 of the flow through cell 301 may be 20 mm to 25 mm. The second variation may be a small flow through cell 302 (FIG. 3B) with a smaller inner diameter 304 of the flow through cell 302 than the large flow through cell 301. In particular the inner diameter 304 of the flow through cell 302 may have a range between 8 mm to 16 mm at a dosage form accommodation position 305. More particularly, the flow through cell 302 has an inner diameter in a range between 10 mm to 14 mm. Both flow through cells 202 comprise filter chamber 306, wherein a filter may be located. Further the flow through cells 202 may comprise a sieve 307 or a mesh for sieving particles dissolved or non-dissolved in the flow through cell 202.

Figure 4:
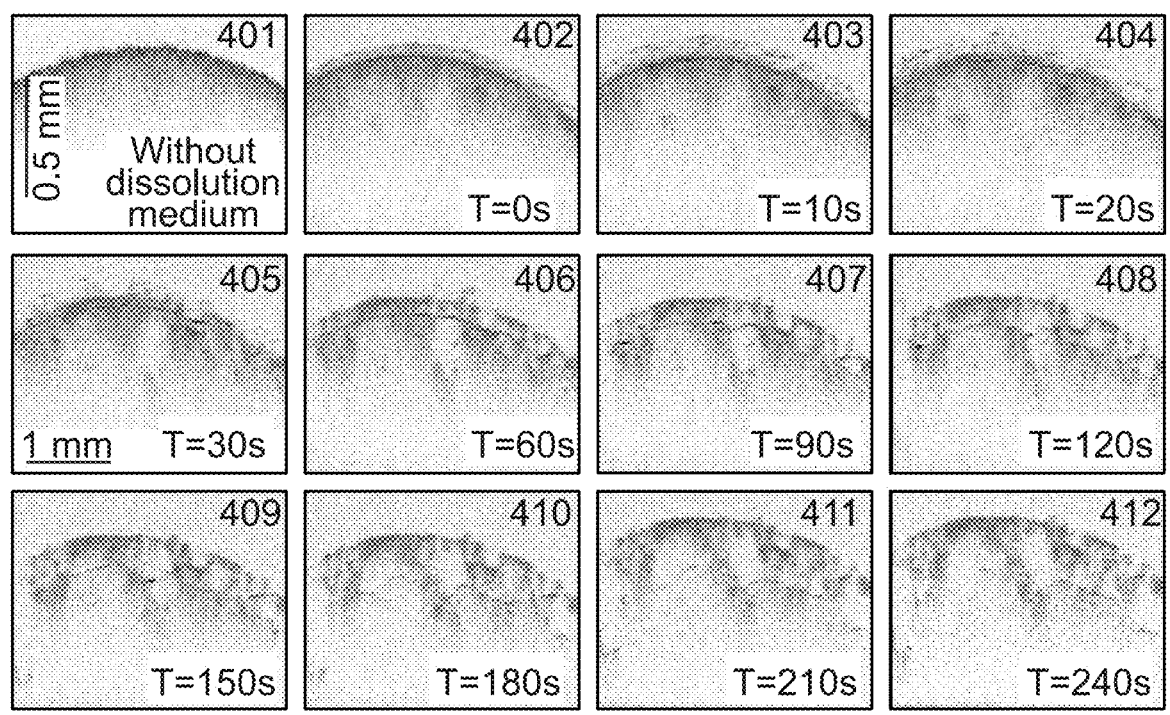
FIG. 4 shows a series of optical coherence tomography images illustrating a dissolution process of a solid dosage form.

In the following, referring to FIG. 4, a series of optical coherence tomography images 401-412 illustrating a dissolution process of a solid dosage form 103 will be described.

These pictures 401-412 describe the dissolution behavior of a Glucophage® film coated tablet during dissolution testing. Glucophage® is a registered trademark of Merck Sante of Lyon, France. This dosage form contains 500 mg of metformin hydrochloride as the active pharmaceutical ingredient and povidone K 30 and magnesium stearate as excipients and the coating contains hypromellose. The dosage form 103 was dissolved in the large flow through cell 301 with turbulent flow in a closed mode system. The closed mode system is a system wherein the flow though cell may be flowed through with a fixed volume flow and the dissolution medium is pumped in a circle. Another possible mode for using a flow though cell may be the open mode. In this configuration fresh dissolution medium may be delivered to the flow though cell and this open configuration may allow for the analysis of extended-release dosage forms. This method may be applied for dosage forms which are hardly soluble. The dissolution medium 104 was water. The pump set at a pump speed of 8 mL/min. The temperature of the medium 104 was the ambient temperature. In the first picture 401 of the left column is shown the dosage form 103 without dissolution medium 104. During the process of dissolution, the structure of the dosage form 103 is changing. As can be seen in the images which relating to different points of time, the changes in and the disintegration of the structure increases. The images show the different structures of the dosage form 103 at different times from 0 seconds, image 402, to 240 seconds, image 412. The swelling of the coating of the dosage form 103 is visible, which can be clearly seen by comparing the image 402 at 0 seconds with the image 407 at 90 seconds. This may be measured with the monitoring apparatus 101 and allows for quantification of the swelling kinetics. The images 405 and further after a time of 20 seconds indicate that the core of the dosage form 103 starts to dissolve and the dissolution and disintegration process are the dominant processes.

Figure 5:
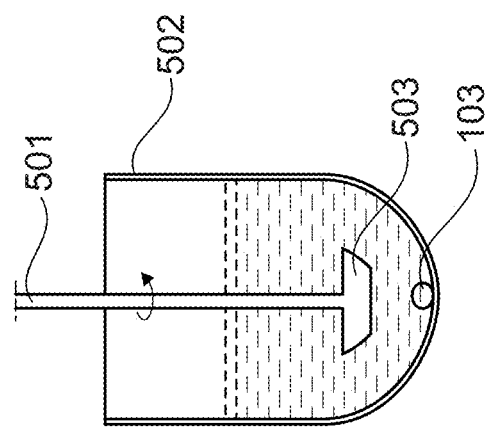
FIG. 5 shows a paddle apparatus according to an exemplary embodiment of the invention.

In the following, referring to FIG. 5 a paddle apparatus will be described. The paddle apparatus may be used as a part of the dissolution device. The paddle apparatus comprises a vessel 502 in which the dosage form 103 and the dissolution medium are located. For dissolving the dosage form a stirrer 501 with a blade 503 are used.

Figure 6:
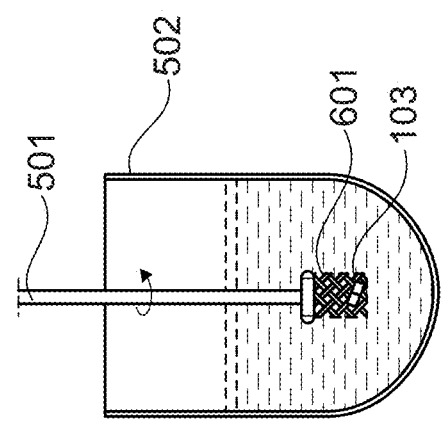
FIG. 6 shows a basket apparatus according to an exemplary embodiment of the invention.

In the following, referring to FIG. 6 a basket apparatus will be described. The basket apparatus may be used as a part of the dissolution device for dissolving the dosage form 103. The basket apparatus comprises a vessel 502 and a stirrer 501. At the stirrer 501 a basket 601 comprising a mesh is arranged. In the basket 601 the dosage form 103 is located.

Figure 7:
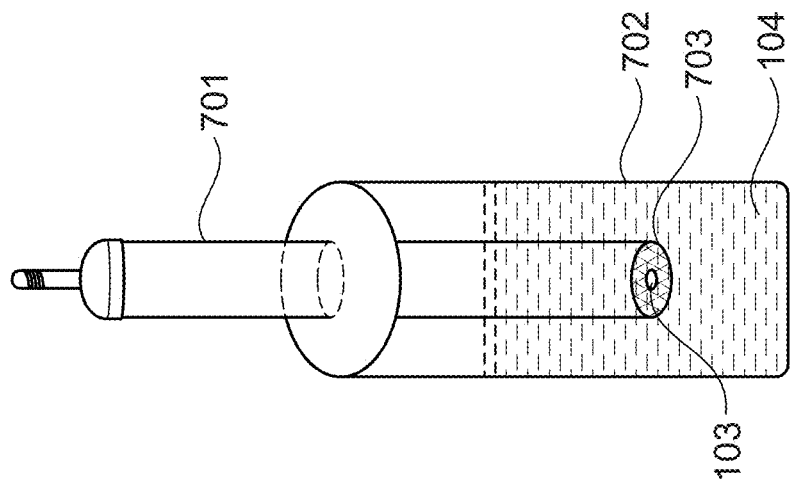
FIG. 7 shows a reciprocating cylinder according to an exemplary embodiment of the invention.

In the following, referring to FIG. 7 a reciprocating cylinder will be described. The reciprocating cylinder may be used as a part of the dissolution device for dissolving the dosage form 103. The reciprocating cylinder may comprise a reciprocating cylinder 701 comprising the dosage form 103 and screens 703 at the top and the bottom of the cylinder 701. The reciprocating cylinder 701 is arranged in a vessel 702 comprising the dissolution medium 104. For dissolving the dosage form 103 the reciprocating cylinder is moved up and down in the vertically direction.

It should be noted that the term "comprising" does not exclude other elements or steps and the "a" or "an" does not exclude a plurality. Also elements described in association with different embodiments may be combined.

Implementation of the invention is not limited to the preferred embodiments shown in the figures and described above. Instead, multiplicities of variants are possible which use the solutions shown and the principle according to the invention even in the case of fundamentally different embodiments.

The invention claimed is:

1. A method of monitoring a property of a dissolution of an at least partially solid dosage form during a dissolution process, the method comprising:
   placing the at least partially solid dosage form in a dissolution apparatus comprising a flow through cell with an opening,
   at least partially dissolving the partially solid dosage form,
   supplying electromagnetic radiation from a sensor head of a monitoring apparatus to the at least partially solid dosage form in the dissolution apparatus with an electromagnetic radiation supply element that extends through the opening into the dissolution apparatus, such that the electromagnetic radiation is getting in contact with the partially solid dosage form to be monitored, and
   during the dissolution of the partially solid dosage form, simultaneously monitoring the property of the dissolution of the dosage form in progress by low coherence interferometry.

2. The method according to claim 1,
   wherein the low coherence interferometry comprises one of the group consisting of a white light interferometry, and an optical coherence tomography.

3. The method according to claim 1,
   wherein the property of the dissolution is monitored by analyzing an obtained interference pattern of the low coherence interferometry.

4. The method according to claim 1,
   wherein the property of the dissolution is at least one of the group consisting of a diffusion behavior of the at least partially solid dosage form during dissolution, a swelling kinetics of the at least partially solid dosage form during dissolution, a swelling of a coating during dissolution, a porosity of the at least partially solid dosage form during dissolution, a structural change of the at least partially solid dosage form during dissolution, a disintegration behavior of the at least partially solid dosage form during dissolution, a water penetration behavior of the at least partially solid dosage form during dissolution, a thickness reduction of a coating of the at least partially solid dosage form during the dissolution, a thickness variation of a coating of the at least partially solid dosage form during dissolution, a thickness variability of a coating of the at least partially solid dosage form during dissolution, an erosion of a coating of the at least partially solid dosage form during dissolution, an erosion of a core of the at least partially solid dosage form during dissolution, a dissolution of particles of a core of the at least partially solid dosage form during dissolution, a formation of a gel layer during dissolution, a formation of an osmotic layer during dissolution, a release of active pharmaceutical ingredient of the at least partially solid dosage form during dissolution, a breaking of a shell of the at least partially solid dosage form during dissolution, a wetting of powder of the at least partially solid dosage form during dissolution, a dispersion behavior during dissolution, a release of liquid content of the at least partially solid dosage form during dissolution, a self-emulsification of at least part of the at least partially solid dosage form during dissolution, a permeation of dissolution medium into the at least partially solid dosage form during dissolution, a diffusion of a drug substance of the at least partially solid dosage form into a dissolution medium, and a cracking behavior of a coating of the at least partially solid dosage form during dissolution.

5. The method according to claim 1,
   wherein the at least partially solid dosage form is one of the group consisting of a tablet, a granulate, a powder, a pellet, a capsule, a gel, a paste, a cream, a suppository, a pessary, a film, a patch, an implant, a polymeric matrix, and an extrudate.

6. The method according to claim 1,
   wherein the property of the dissolution is monitored in a contactless manner.

7. The method according to claim 1,
wherein information indicative of the property is detected in a plurality of consecutive time intervals or continuously in time.

8. The method according to claim 1,
wherein the monitoring is conducted in the framework of an at least partially solid dosage form manufacturing process.

9. The method according to claim 1,
wherein the monitoring is conducted while the at least partially solid dosage form is changing a dosage form constitution, and
wherein the monitoring is conducted by an in-line process.

10. The method according to claim 1, further comprising:
correlating of the monitored property of the dissolution with a pharmacokinetic characteristic.

11. A device for dissolving a partially solid dosage form and monitoring a property of the dissolution of the partially solid dosage form during a dissolution process, the device comprising:
a dissolution apparatus configured for at least partially dissolving the partially solid dosage form, wherein the dissolution apparatus comprises a flow through cell;
a monitoring apparatus configured for monitoring the property of the dissolution of the partially solid dosage form during dissolving the partially solid dosage form by the dissolution apparatus,
wherein the monitoring apparatus is configured for monitoring the property of the dissolution of the partially solid dosage form simultaneously with and during a dissolution process using low coherence interferometry; and
an electromagnetic radiation supply element configured for supplying electromagnetic radiation from a sensor head of the monitoring apparatus to the partially solid dosage form in the dissolution apparatus, such that the electromagnetic radiation is getting in contact with the partially solid dosage form to be monitored;
wherein the electromagnetic radiation supply element extends from the sensor head to the partially solid dosage form, and
wherein the electromagnetic radiation supply element extends through an opening of the flow through cell into the dissolution apparatus.

12. The device according to claim 11,
wherein at least a part of the monitoring apparatus is located so as to have insight in an interior of the dissolution apparatus, the interior accommodating the partially solid dosage form to be dissolved and comprising a volume in which the dissolving of the partially solid dosage form occurs.

13. The device according to claim 11,
wherein the monitoring apparatus and the dissolution apparatus are configured for guiding primary electromagnetic radiation from the monitoring apparatus into the dissolution apparatus and for guiding secondary electromagnetic radiation, generated by an interaction between the primary electromagnetic radiation and the partially solid dosage form during dissolution, from the dissolution apparatus into the monitoring apparatus.

14. The device according to claim 11,
wherein the dissolution apparatus comprises at least one of the group consisting of a basket apparatus, a paddle apparatus, a reciprocating cylinder, an intrinsic dissolution system, a Franz cell, and a membrane dissolution system.

15. The device according to claim 11,
wherein a medium in which the partially solid dosage form is dissolved during the dissolution process comprises at least one of the group consisting of water, one or more buffers, a biorelevant medium, and a viscous medium.

16. The device according to claim 11,
wherein the flow through cell has an inner diameter at an accommodation position in a range between one of the group consisting of 17 mm to 30 mm and 8 mm to 16 mm.

17. The device according to claim 11,
wherein the dissolution apparatus comprises at least one pump for pumping at least one of a dissolution medium and a heating medium.

18. The device according to claim 11,
wherein the device comprises a control unit adapted to direct the dissolution apparatus to at least partially dissolve the partially solid dosage form, and during the dissolution of the partially solid dosage form, simultaneously direct the monitoring apparatus to monitor the property of the dissolution of the partially solid dosage form in progress by low coherence interferometry.

* * * * *